United States Patent [19]

Kikabhai

[11] Patent Number: 5,087,761
[45] Date of Patent: Feb. 11, 1992

[54] SYNTHESIS OF ALPHA-HYDROXY KETONES

[75] Inventor: Thakor Kikabhai, North Humberside, England

[73] Assignee: BP Chemicals Limited, London, England

[21] Appl. No.: 550,334

[22] Filed: Jul. 6, 1990

[30] Foreign Application Priority Data

Jul. 26, 1989 [GB] United Kingdom ............... 8917092

[51] Int. Cl.$^5$ ............................................. C07C 45/45
[52] U.S. Cl. ................................. 568/388; 568/312
[58] Field of Search ................. 568/388, 387, 312

[56] References Cited

U.S. PATENT DOCUMENTS

| 4,301,310 | 11/1981 | Wagner | 568/388 |
| 4,782,186 | 11/1988 | Beevor | 568/388 |

FOREIGN PATENT DOCUMENTS

| 274226 | 7/1986 | European Pat. Off. |
| 219317 | 4/1987 | European Pat. Off. |
| 245976 | 11/1987 | European Pat. Off. |
| 306215 | 8/1989 | European Pat. Off. |
| 59-164745 | 9/1984 | Japan | 568/388 |
| 59-164746 | 9/1984 | Japan | 568/388 |
| 60-184038 | 9/1985 | Japan | 568/388 |
| 01085944 | 3/1989 | Japan | 568/388 |
| 634029 | 1/1983 | Switzerland |

OTHER PUBLICATIONS

Gracey et al., Chem. Abst., vol. 111, #233473g (1989).
Tanaka et al., Chem. Abst., vol. 111, #136, 456W (1989).
European Search Report dated Feb. 13, 1990 for application number EP 90307663.6 which is the counterpart in Europe to the present application.
Matsumoto et al., J. Chem. Soc. Chem., Commun. (1983), pp. 171-172.

*Primary Examiner*—James H. Reamer
*Attorney, Agent, or Firm*—Brooks Haidt Haffner & Delahunty

[57] ABSTRACT

This invention relates to a process for condensing aldehydes to alpha-hydroxyketones in a liquid system containing an aldehyde and an active condensation catalyst formed by the abstraction of HX from a thiazolium salt in which X is the anion. The reaction is carried out in the absence of a base (other than the active catalyst) and the anion X. The catalyst is rendered free of the undesirable base and the anion X because these are the cause of premature deactivation of the catalyst.

16 Claims, No Drawings

SYNTHESIS OF ALPHA-HYDROXY KETONES

This invention relates to a process for the production of alpha-hydroxy ketones, especially dihydroxy acetone and the use thereof for producing glycerol.

Dihydroxy acetone is a valuable raw material for the production of alcohols and esters, especially glycerol which in turn is used to produce various esters, printing inks, foodstuffs, in antifreezes, as a moistening agent in tobacco, in soaps and for producing nitroglycerine.

Our published EP-A-306215 describes a process for synthesising glycerol by initially self condensing formaldehyde in a substantially anhydrous state to dihydroxy acetone (hereafter DHA) followed by hydrogenation of the DHA. In this document, and in other prior published documents on self condensation reaction such as the article by Matsumoto, T. et al in J.A.C.S., 1984, 106, pp 4289-4832 and in EP-A-245976, the self condensation stage has invariably been carried out in the presence of a base such as triethyl amine and halide ions such as bromides. The bromide ions come from the salt of the heterocyclic catalyst such as the thiazolium bromide used. However, these processes have been commercially unattractive because the catalyst used in such processes could not be readily regenerated due to water, a by-product of the process, being a catalyst poison.

It is an object of the present invention to devise a simple route to alpha-hydroxy ketones e.g. DHA from aldehydes such as formaldehyde. A further object of the process is to provide a simple method of regenerating the condensation catalyst which can then be recycled to the reaction.

It has now been found that formaldehyde can be converted to DHA at significant rates and in good selectivities and yields to make an integrated process to glycerol commercially attractive.

Accordingly, the present invention relates to a process for condensing aldehydes to alpha-hydroxy ketone in a liquid reaction system comprising at least one aldehyde and an active condensation catalyst formed by the abstraction of HX from a thiazolium salt in which X represents the anion, characterised in that the reaction is carried out in the substantial absence of (a) a base other than the active catalyst and (b) the anion X.

By "an active condensation catalyst" is meant here and throughout the specification that a thiazolium salt catalyst is activated by abstraction of HX from said salt prior to the commencement of the reaction.

By "substantial absence of (a) a base other than the active catalyst and (b) the anion X" as used herein is meant that the liquid condensation reaction system contains less than 0.5 molar equivalents preferably less than 0.1 molar equivalent of either based on the active catalyst during the condensation reaction. The term "based" as used herein is primarily but not solely directed to the use of amine bases such as e.g. triethylamine.

A feature of the invention is that the reaction is achieved in the substantial absence of any base (other than the catalyst) or the anion X. It has been found that the substantial removal of these components from the reaction system not only allows the reaction to be carried out over a much longer duration without loss of the desired alpha-hydroxy ketone product by further undesirable reactions but also (i) improves the selectivity to the desired product and (ii) facilitates purification of the DHA.

The abstraction of HX from the thiazolium salt to form the active catalyst renders the reaction system substantially free of any undesirable base or the anion X prior to the commencement of the condensation reaction. This may be carried out on the thiazolium salt alone or on the total reaction system inclusive of the reactant aldehyde in several ways.

The active catalyst can be generated by vigorous agitation of the thiazolium salt with an aqueous-alcoholic mixture in which the alcohol component is either immiscible with or only partially miscible with water. The resultant mixture can then be allowed to separate into aqueous and alcoholic phases whereby the active condensation catalyst will remain in the alcohol phase and the undesirable bases and the anion X will remain in the aqueous phase. Where a system comprising the thiazolium salt washed also contains the aldehyde reactant, some of the aldehyde may be inevitably lost due to partitioning. In such a case a supplemental amount of the aldehyde may have to be added to the washed reaction system. The alcohol phase can then be used directly to carry out the condensation reaction.

Alternatively an active catalyst can be generated without adding any dissolved base, using instead a bed or slurry of basic ion exchange resin to produce the required activation. The activated catalyst solution is then either eluted or decanted from the resin. This basic ion exchange resin has the additional ability to remove the anion X from the catalyst solution by producing a halide salt form of the resin.

The resultant eluate from the resin bed, substantially free of both the anion X and unwanted base, can be used for the condensation reaction, if necessary after the removal of excess water and/or alcohol by distillation.

A further feature of the present invention is that the aldehyde reactant used can be hydrous or anhydrous prior to the commencement of condensation. However, during the actual condensation reaction, it is important to remove as much of the water from the reaction system as is practicable to achieve optimum results. Ideally, the reactants should be substantially dry, i.e. substantially free of water to maximise catalyst activity. One method of achieving such an objective is to use for the reaction e.g. a distillation still in which water is continually removed overhead whereas the reaction occurs at the bottom of the still, the so called "kettle" of the still. The removal of water can also be aided by the use of e.g. an azeotroping agent such as an alcohol, ether or a hydrocarbon, especially cyclohexane. Alternatively, water can be removed from the reaction system by the use of a reactor capable of reduced pressure evaporation.

A significant advantage of the present process is that water, a known catalyst poison for this reaction, can be removed continuously from the system in this manner. This method has been possible only due to our surprising observation that the poisoning of the catalyst by water is a reversible reaction. Thus, the continuous removal of water from the system has the added benefit of regenerating the catalyst thereby enabling recycle of the regenerated catalyst to the condensation stage. It may be necessary in some cases to supplement any such recycled catalyst with one or more of the essential components in order to maintain a uniform catalyst concentration throughout the reaction.

Thus, if the aldehyde used is formaldehyde, it may be used in monomeric, oligomeric or polymeric form. In monomeric form it may be used either as formaldehyde gas or as a solution of formaldehyde in an organic solvent, suitably an alkanol, for example methanol, ethanol or propanol, butanol, cyclohexanol, methylisobutyl carbinol, 2-ethyl hexanol, glycols, polyols such as glycerol or a mixture thereof.

The source of the active catalyst is suitably a thiazolium salt of anion X. It is preferably an aliphatic, aromatic or a heterocyclic thiazolium salt of the anion X. The anion X may be any anion capable of forming a salt with the thiazolium cation. Specific examples of such anion X include the halides, the sulphates and the carboxylates but is preferably a halide and is especially a bromide. Of these the 3-methyl benzothiazolium bromide, 3-ethylbenzothiazolium bromide, 3-laurylbenzothiazolium bromide, 3-isopropylbenzothiazolium bromide, 3-butylbenzothiazolium bromide and 3-ethyl thiazolium bromide are specific examples. The thiazolium ion is chosen so as to offer an optimum combination of catalyst activity and ease of separation from the desired hydroxyacetone product.

The relative molar ratios of aldehyde to the condensation catalyst in the initial reaction mixture may vary over a wide range. Use of excess catalyst is not detrimental to the reaction or the economics of the process since the catalyst can be regenerated and reused. Thus the mole ratio of the aldehyde reactant to catalyst can be as low as 3:1 or as high as 10000:1.

The liquid medium used in the reaction system is preferably a (cyclo) aliphatic alcohol. The (cyclo) aliphatic alcohol solvent for the condensation step is suitably a solvent or mixtures of solvents capable of dissolving the reactant aldehyde and/or the active condensation catalyst in the system. In a homogeneous system clearly the solvent will dissolve both. It is essential, however, that the alcohol is either immiscible with or only partially miscible with water. The alcohol should not be totally miscible with water. Specific examples of the solvents that can be used include the aliphatic alcohols, e.g. the butanols, methylisobutyl carbinol, 2-methyl pentanol and 2-ethyl hexanol.

A feature of the present invention is that the reaction system is substantially freed from bases (other than the active catalyst) and the anion X prior to the commencement of the condensation reaction. This is achieved by washing the reaction system containing the aldehyde reactant and the thiazolium salt e.g. with an aqueous-alcoholic mixture. The ratio of alcohol to water in the aqueous-alcoholic mixture used, if such is used to remove bases and halide ions, for washing the reaction system prior to the commencement of the condensation reaction is suitably from 1:1 to 100:1. For 2-ethyl hexanol this range is preferably from 2:1 to 7:1 by volume.

The alcohol used in this mixture is also either immiscible or only partially miscible with water but should not be totally miscible with water. The alcohol used in this case may be the same as or different from that used as the liquid medium for the condensation reaction.

The reaction system is suitably washed at a temperature below 80° C., preferably at ambient temperature in order to minimise loss of aldehyde values e.g. to the aqueous stream during phase separation.

Alternatively or additionally, the anion X such as e.g. halide ions can be removed or further removed by passage of the reaction system over a basic ion exchange resin bed. The rate of flow over such a bed is suitably between a linear hourly space velocity of 0.1/h to 50/h more preferably between 0.5/h and 10/h. The particular space velocity chosen depends both on the degree to which it is desired to remove halide ions and upon the particular thiazolium salt used.

The ion exchange treatment is conducted below 100° C. preferably at ambient temperature. Suitable resins for this treatment are readily available and typical examples include but are not restricted to Amberlyst 21 (a weakly basic macroreticular polystyrene resin ex Rohm and Haas) or Amberlyst 26 (a strongly basic macroreticular polystyrene resin ex Rohm and Haas) (Regd Trade Marks).

The ion exchange treatment described is capable of reducing the halide content of the reaction system to below 2 ppm by weight if so desired.

One particularly preferred method of rendering the reaction system free of undesirable bases and the anion X e.g. halide ions, is to make use of the basic functional groups on a basic ion exchange resin to activate the thiazolium salt simultaneously with the removal of halide ions. In this way there is no requirement for additional amine species e.g. triethylamine to be added to the reaction system at any time.

The thus prepared reaction system is then subjected to condensation.

The condensation reaction can be a self-condensation or cross-condensation. In the case of the latter at least two aldehyde reactants should be present. The self-condensation is preferably carried out with formaldehyde and in this case the product is dihydroxy acetone (hereafter referred to as such or as "DHA" for convenience). The self-condensation of formaldehyde is suitably carried out at a temperature from 20°–200° C., preferably from 80°–170° C., most preferably from 100°–120° C. It will be appreciated that the reaction is exothermic and hence reactions initiated within this range may, during the reaction, exceed the preferred upper limit of 170° C. specified herein. The reaction pressure may be reduced, ambient or elevated provided that the pressure is controlled to maintain the reactants and/or solvents substantially in the liquid state.

The self-condensation product containing dihydroxy acetone as such, as a dimer thereof or as a mixture of the two can be separated from the catalyst components by conventional means e.g. by one or more of the following: precipitation, dialysis, liquid-liquid extraction, membrane separation such as hyperfiltration, distillation (whether or not under vacuum) e.g. steam stripping, and the use of adsorbent materials such as ion exchange resins.

In the case of certain solvents, e.g. alcoholic solvents such as 2-ethyl hexanol, used in the self-condensation stage, the dihydroxy acetone formed can be separated from the reaction mixture simply by cooling whereby the dihydroxy acetone precipitates. The remaining liquid phase can be optionally recycled to the condensation reactor or further processed in the separation stage. Precipitation can be made to occur so as to recover a greater proportion of the dihydroxyacetone or its dimer than is achieved simply by cooling. One method is to reduce the volume of the solvent present by distillation and then cool the remaining solution. An alternative approach is to remove essentially all of the solvent to give a solid or a viscous liquid phase. This phase is then redissolved in a solvent from which dihydroxyacetone or its dimer can be readily precipitated either by cooling or by the addition of a second liquid component such as e.g. additions of diethyl ether or 2-ethylhexanol to a solution of the viscous phase in acetone.

Under certain temperature or dihydroxyacetone concentration regimes it is possible to substantially separate the dihydroxyacetone from the reaction solvent as a liquid phase precipitation. A dihydroxyacetone rich liquid phase can thus be removed for further processing leaving a solvent rich phase for recycle to the condensation stage.

If it is intended to use liquid-liquid extraction as the separation method, then water can be used as the extractant to preferentialy extract dihydroxyacetone from reaction solvents such as 2-ethyl hexanol. In this case, the efficiency of separation of dihydroxyacetone can be improved by using as catalyst a thiazolium salt bearing large aliphatic groups thereby enhancing the partition of the catalyst into the organic phase.

Adsorbent materials may also be used to remove the catalyst system from the reaction products either alone or in combination with any one of the above methods. Typical adsorbents include activated carbons, alumina, silica, metal oxides, supported metals on carbon or metal oxide and ion exchange resins. With certain adsorbent materials, it can be advantageous to regenerate the adsorbent, for example by heating the adsorbent in a suitable atmosphere such as hydrogen, steam or air. Adsorbent treatments are particularly suitable for use in combination with a treatment such as liquid-liquid extraction.

The DHA so recovered is suitable for use particularly as a source of glycerol upon hydrogenation.

It is a feature of the invention that, depending upon the method of recovery of DHA, the sulphur, nitrogen and halogen containing components can be substantially absent from the reaction products of the condensation step, and hence the remaining products containing crude dihydroxy acetone need not be further purified prior to use in the hydrogenation step for converting DHA to glycerol. One such method where the crude DHA product can be used directly for hydrogenation to glycerol is that recovered by crystallisation.

As regards the hydrogenation step, the dihydroxyacetone can be hydrogenated in the presence of a hydrogenation catalyst and hydrogen. The hydrogenation catalyst may be a heterogeneous or a homogeneous hydrogenation catalyst.

Where the catalyst is a heterogeneous hydrogenation catalyst it is suitably a finely divided or a supported Group VIII metal. For example such a catalyst may be nickel, Raney nickel or ruthenium supported on a support inert under the reaction conditions e.g. carbon or graphite, or copper chromite type catalyst. Where the hydrogenation catalyst is a homogeneous catalyst, such a catalyst is soluble in the liquid reaction medium and is suitably a compound or mixture of compounds containing a noble metal moiety (i) and a moiety (ii) of the formula $QR_3$ wherein Q is either phosphorus, arsenic or antimony and the groups R are independently either hydrogen or hydrocarbyl or substituted hydrocarbyl groups. Throughout this specification the term noble metal means platinium, palladium, rhodium, ruthenium, iridium or osmium. Of the noble metals, palladium, platinum, rhodium and ruthenium are preferred. Preferably Q in the formula is phosphorus. The group R in the formula is preferably a hydrocarbyl or substituted hydrocarbyl group. Suitable hydrocarbyl groups include alkyl groups, cycloalkyl groups and aryl groups, which may be substituted or unsubstituted. The catalyst may suitably combine the moieties (i) and (ii) in a single compound, for example as the compound $RhCl(PPh_3)_3$ or the compound $Ru(H)(OAc)(PPh_3)_3$. Alternatively, the moities (i) and (ii) may be added in the form of separate compounds for example as $RhCl_2$ and $PPh_3$ to form the hydrogenation catalyst in situ.

Where the catalyst is a homogenous hydrogenation catalyst, particularly when this takes the form of a single compound, it may be supported on a suitable support. Such supports include organic polymers, for example polystyrene containing the appropriate functional moiety (ii).

Hydrogen is readily available on a commercial scale. It may be used in a commercially available form or may, if desired, be further purified. The hydrogen partial pressure is suitably in the range from 10 to 30,000 KPa, preferably from 100 to 5000 KPa.

The hydrogenation of DHA may be accomplished at elevated temperature, suitably in the range from ambient to 150° C., preferably from 40° to 150° C., most preferably from 40° to 120° C.

The liquid reaction medium for the hydrogenation step is suitably a solvent capable of dissolving the hydrogenation reactants and, in the case of a homogeneous reaction, the catalyst. Suitable solvents include, but are not restricted to, alcohols, water, ethers and mixtures of one or more of these. The particular solvent of preference may be advantageously the same as that chosen for the self condensation step (c).

The hydrogenation of DHA may suitably be carried out batchwise or continuously, preferably continuously.

For a batch operation, the duration of the hydrogenation reaction will vary with the type and concentration of the hydrogenation catalyst, the hydrogen partial pressure and with the nature of the product being hydrogenated, i.e. whether crude or pure or whether the reaction is carried out in situ. The glycerol product formed upon hydrogenation can be purified and recovered by methods well known in the art. A suitable method of purification is vacuum distillation. If required post treatments known to those skilled in the art may be used. Such treatments include, but are not restricted to, passage over a carbon bed and treatment with bleaching agent.

The present process is clearly simpler and less expensive to operate than the synthetic processes used hitherto. The raw materials are easily available and the products easily separated and purified.

The present invention is further illustrated with reference to the following Examples.

EXAMPLE 1

This Example demonstrates the continuous condensation reaction following extraction of nitrogen containing bases and bromide prior to the reaction.

3-Ethylbenzothiazolium bromide (0.9025 g) was dissolved, by use of a magnetic follower, into a solution (616.2 g) comprising 18 wt % formaldehyde (HCHO) in 2-ethylhexanol (2EH) over a period of 20 mins (40° C.). The mixture was allowed to cool to ambient temperature before triethylamine (TEA, 0.36 g) was added. The solution was further stirred (30 mins, ambient temperature) before 500 ml was extracted with 100 ml deionised water, to remove base and bromide (1 min contact time, manual shaking, 3 days settling time at ambient temperature). Typically, water extraction removes >98% bromide and Ca. 50% N-base from the original organic reactant stream demonstrating the removal of TEA base and bromide by this method. The organic layer (150.2 g) was charged to 250 ml flask. The system was purged with nitrogen and heated (105° C.) such that an organic/water azeotrope was continually removed from the flask by azeotropoic distillation, the reaction flask was fitted with a rubber septum to allow samples to be withdrawn using a syringe. The reaction was monitored by gas-liquid chromatography, high pressure liquid chromatography and Karl Fischer. The following results were obtained:

| TIME (MINUTES) | FORMAL-DEHYDE (% W/W) | DIHYDROXY-ACETONE (% W/W) | WATER (% W/W) |
| --- | --- | --- | --- |
| 0 | 17.2 | <0.1 | 3.5 |
| 15 | 17.4 | <0.1 | 3.3 |
| 30 | 17.1 | <0.1 | 3.1 |
| 60 | 17.6 | <0.1 | 1.98 |
| 120 | 16.5 | 0.16 | 0.9 |
| 180 | 15.8 | 0.51 | 0.4 |
| 240 | 13.7 | 1.70 | 0.3 |
| 300 | 9.9 | 4.23 | 0.3 |
| 360* | 6.9 | 7.0 | 0.24 |

*Precipitation of DHA occurs on cooling to ambient temperature.

EXAMPLE 2

This Example demonstrates the use of ion exchange resins to remove bromide and activate the catalyst prior to reaction. It also demonstrates recycling of the catalyst following removal of product by water extraction.

A product stream was generated by passing a reactant stream comprising 3-ethylbenzothiazolium bromide (0.6 mmol per 100 g solvent) and 26 wt % formaldehyde (HCHO) in 2-ethylhexanol (2EH), through a bed of Amberlyst A21 weakly basic ion exchange resin (10 g dry weight) at a range of temperatures between 30°-90° C. using a flow rate of 35-40 ml/hr and heating the mixture thereafter (30 mins at 117° C.). Typically, with a resin bed temperature of 40° C., selectivity to dihydroxyacetone (DHA) is 96%, selectivity to erythrulose hydrate is 4% and HCHO conversion is 12%. In addition, following treatment with ion exchange bed, the level of bromide is reduced from 504 ppm (w/w) to 4 ppm (w/w) demonstrating the ability of the resin to remove bromide from the reaction stream. The resin bed was pretreated by drying 15 g of Amberlyst A21 in vacuo, pre-swelling overnight in the HCHO/2EH solution and washing with 2EH prior to the experiment. The pretreated resin was packed into a glass column and between 10 ml sections of glass beads. The column was chosen such that the length:diameter ratio was >10.

A sample was prepared using a resin bed temperature of 70° C. The product stream comprised 1.85 wt % dihydroxyacetone (DHA) and 0.2 wt % erythrulose hydrate. The product stream was extracted with water to remove DHA and erythrulose hydrate (2 successive extractions; ratio product stream:water=5:1 v/v, 1 min contact time, manual shaking, 1 day settling time). The organic layer (215.3 g) containing the recycled catalyst was transferred to a 500 ml flask, purged with nitrogen and heated (106°-7° C.) such that an organic/water azeotrope was continuously removed from the system. The reaction was regularly sampled by withdrawal by syringe through a septum fitted to the reaction flask. The following results were obtained.

| TIME (MINUTES) | FROMAL-DEHYDE (% W/W) | DIHYDROXYACETONE (% W/W) |
| --- | --- | --- |
| 0 | 21.6 | <0.1 |
| 15 | 21.39 | <0.1 |
| 30 | 20.97 | <0.1 |
| 60 | 20.6 | <0.1 |
| 120 | 19.09 | <0.1 |
| 180ᵃ | 11.17 | 1.25 |
| 270ᵇ | 6.49 | 6.03 |
| 300ᵇ | 5.65 | 9.30 |
| 370ᵇ | 4.6 | 11.02 |
| 420ᵇ | 4.20 | 11.95 |

ᵃSolution was pale yellow.
ᵇSolution was yellow, white precipitate (DHA) appeared on cooling.

EXAMPLE 3

This Example demonstrates removal of bromide by aqueous extraction and performance of the condensation reaction in the absence of a nitrogen base other than the activated catalyst.

3-ethylbenzothiazolium bromide (0.3662 g) was dissolved, by use of a magnetic follower, into a solution of 18 wt % formaldehyde (HCHO) in 2-ethylhexanol (2EH) (250 g) over a period of 20 mins at 40° C. The mixture was allowed to cool to ambient temperature and extracted with water (ratio organic:water=5:1 v/v, 1 min contact time, manual shaking, 3 days settling time). The organic layer was found to comprise <4 ppm (w/w) bromide demonstrating the use of water extraction to remove bromide. The organic layer (116.7 g) was charged to a 250 ml flask, purged with nitrogen and heated (106°-7° C.) such that an organic/water azeotrope was continuously removed from the system by azeotropic distillation. The reactor was sampled as described in Example 1 and the following results were obtained:

| TIME (MINUTES) | FORMAL-DEHYDE (% W/W) | DIHYDROXY-ACETONE (% W/W) | WATER (% W/W) |
| --- | --- | --- | --- |
| 0 | 14.2 | <0.1 | 3.35 |
| 30 | 14.3 | <0.1 | 2.57 |
| 60 | 14.3 | <0.1 | 0.619 |
| 120 | 10.7 | 2.42 | 0.10 |
| 170 | 7.2 | 5.48 | 0.061 |
| 230 | 4.92 | 6.87 | 0.05 |
| 300 | 3.8 | 7.21 | 0.06 |
| 360 | 3.30 | 7.70 | 0.059 |

Note:
Detection limit for DHA using high pressure liquid chromatography is 0.1 wt %.

EXAMPLE 4

The ion exchange activation procedure of Example 2 was followed using isobutanol in place of 2-ethyl hexanol. The reaction system produced was refluxed in a vacuum still at pressures between 300 mmHg and atmospheric pressure, water being removed from the system azeotropically. DHA was produced with selectivities ranging between 85 and 90%, the main byproduct being erythrulose hydrate.

EXAMPLE 5

The ion exchange activation procedure of Example 2 was followed using a mixture of isobutanol and methylisobutylcarbinol in place of 2-ethyl hexanol. The reaction system produced was refluxed in a vacuum still at pressures between 300 mmHg and atmospheric pressure, water being removed from the system azeotropically. DHA was produced with a selectivity around 90%, the main byproduct being erythrulose hydrate.

EXAMPLE 6

The ion exchange activation procedure of Example 2 was followed using a mixture of propanol and methylisobutylcarbinol in place of 2-ethyl hexanol. The reaction system produced was refluxed in a vacuum still at pressures between 300 mmHg and atmospheric pressure, water being removed from the system azeotropically. DHA was produced with selectivities above 90%, the main byproduct being erythrulose hydrate.

EXAMPLE 7

This Example demonstrates that a separation of reaction products and catalyst can be readily achieved by aqueous extraction of the reaction product.

Reaction product mixture containing DHA, erythrulose hydrate, formaldehyde, methylisobutylcarbinol, isobutanol and activated 3-ethylbenzothiazolium but free of halide ions and other amine species was liquid extracted with water. Extractions with ratios of organic phase to water between 5:1 and 1:5 established that the DHA and other condensation reaction products partition into the water phase with a mass partition ratio of around 10:1. The benzothiazolium in contrast showed a mass partition ratio of 1:9 in favour of the organic phase.

COMPARATIVE TEST 1

This is not an example according to the invention but is included to demonstrate the difficulty of separating DHA from bases and halide ions when halide ions are present in the reaction.

DHA was produced by heating a mixture containing 2-ethylhexanol, formaldehyde, 3-ethylbenzothiazolium bromide and triethylamine in a stoichiometric equivalent to the thiazolium salt. The product was then extracted with water using an organic to water ratio of 3:1. Over 90% of the bromide ions transferred with the DHA into the aqueous phase, substantially as triethylammonium bromide.

I claim:

1. A process for condensing aldehydes to alpha-hydroxyketones in a liquid reaction system comprising at least one aldehyde and an active condensation catalyst formed by the abstraction of HX from a thiazolium salt in which X represents the anion, characterised in that the reaction is carried out in the substantial absence of
   (a) a base other than the active catalyst and
   (b) the anion X.
2. A process according to claim 1 wherein the reaction system is rendered substantially free of the base or the anion X prior to the commencement of the reaction.
3. A process according to claim 1 wherein a thiazolium halide is used as the source of the active catalyst.
4. A process according to claim 1 wherein the active catalyst is rendered substantially free of the undesirable base and/or the anion X by eluting a solution of the thiazolium salt over a basic ion exchange resin capable of adsorbing the undesirable base or the anion X and using the eluate in the reaction system.
5. A process according to claim 1 wherein the catalyst is rendered substantially free of base and the anion X by extracting a catalyst system, which is the source of the active catalyst with an aqueous alcoholic mixture in which the alcohol component is either immiscible with or only partially miscible with water, allowing the resulting mixture to separate into aqueous and alcoholic phases and recovering the catalyst free of base and the anion X from the alcohol phase.
6. A process according to claim 1 wherein the condensation reaction is carried out under substantially dry conditions.
7. A process according to claim 6 wherein the reaction is carried out in a distillation still in which water is continually removed overhead whereas the reaction takes place at the bottom of the still.
8. A process according to claim 7 wherein the removal of water is aided by the use of an azeotroping agent.
9. A process according to claim 1 wherein the relative molar ratios of aldehyde to the condensation catalyst in the initial reaction mixture is from 3:1 to 10000:1.
10. A process according to claim 1 wherein the aldehyde reactant is formaldehyde.
11. A process according to claim 1 wherein the source of the active catalyst is selected from an aliphatic, aromatic and heterocyclic thiazolium halide salt.
12. A process according to claim 1 wherein the liquid medium in the reaction system is a (cyclo)aliphatic alcohol.
13. A process according to claim 12 wherein the (cyclo)aliphatic alcohol is capable of dissolving the reactant aldehyde and/or the condensation catalyst in the system but is either immiscible with or is only partially miscible with water.
14. A process according to claim 1 wherein the condensation reaction is carried out at a temperature from 20°–200° C.
15. A process according to claim 1 wherein the product alpha-hydroxyketone is recovered from the reaction mixture by one or more of the following methods: precipitation, dialysis, liquid-liquid extraction, and membrane separation.
16. A process according to claim 1 wherein dihydroxy acetone is produced by the self-condensation of formaldehyde.

* * * * *